United States Patent
Aranyi et al.

(10) Patent No.: US 10,022,142 B2
(45) Date of Patent: Jul. 17, 2018

(54) ULTRASONIC SURGICAL INSTRUMENT

(71) Applicant: Covidien LP, Mansfield, MA (US)

(72) Inventors: Ernest Aranyi, Easton, CT (US); Douglas J. Cuny, Bethel, CT (US); Russell Heinrich, Madison, CT (US); Amit Lal, Ithaca, NY (US); Bill Lewis, Monroe, CT (US); Philip C. Roy, Lafayette, CO (US)

(73) Assignee: Covidien LP, Mansfield, MA (US)

( * ) Notice: Subject to any disclaimer, the term of this patent is extended or adjusted under 35 U.S.C. 154(b) by 284 days.

(21) Appl. No.: 14/989,194

(22) Filed: Jan. 6, 2016

(65) Prior Publication Data

US 2016/0113672 A1    Apr. 28, 2016

Related U.S. Application Data

(63) Continuation of application No. 12/053,113, filed on Mar. 21, 2008, now abandoned, which is a continuation of application No. 10/467,512, filed as application No. PCT/US02/04988 on Feb. 8, 2002, now abandoned.

(60) Provisional application No. 60/267,251, filed on Feb. 8, 2001.

(51) Int. Cl.
  *A61B 17/32*  (2006.01)
  *A61B 17/22*  (2006.01)
  *A61B 17/00*  (2006.01)
  *A61B 17/29*  (2006.01)

(52) U.S. Cl.
  CPC ...... *A61B 17/320068* (2013.01); *A61B 17/29* (2013.01); *A61B 17/320092* (2013.01); *A61B 17/2202* (2013.01); *A61B 2017/00026* (2013.01); *A61B 2017/00084* (2013.01); *A61B 2017/2927* (2013.01); *A61B 2017/320071* (2017.08); *A61B 2017/320072* (2013.01)

(58) Field of Classification Search
  CPC .... A61B 17/320068; A61B 17/320092; A61B 17/29
  See application file for complete search history.

(56) References Cited

U.S. PATENT DOCUMENTS

| | | |
|---|---|---|
| 4,354,628 A | 10/1982 | Green |
| 4,508,253 A | 4/1985 | Green |
| 5,300,081 A | 4/1994 | Young et al. |

(Continued)

FOREIGN PATENT DOCUMENTS

| | | |
|---|---|---|
| EP | 0537570 A2 | 4/1993 |
| EP | 0 647 431 A2 | 4/1995 |

(Continued)

OTHER PUBLICATIONS

European Search Report dated Oct. 23, 2008, issued in EP 08165099.6-2310.

*Primary Examiner* — Tuan V Nguyen

(57) ABSTRACT

An ultrasonic surgical instrument is provided which includes a handle assembly, a body extending distally from the handle assembly and an end effector configured to effect cutting, dissection, coagulation and/or ligation of tissue. The end effector includes an ultrasonic member. A transducer is supported adjacent, on or within the ultrasonic member and is connected to a power source. Upon actuation of the power source, the transducer effects vibration of the ultrasonic member. In one preferred embodiment, the end effector is mounted for articulation about the distal end of the instrument.

18 Claims, 6 Drawing Sheets

(56) References Cited

U.S. PATENT DOCUMENTS

| | | | |
|---|---|---|---|
| 5,322,055 A | 6/1994 | Davison et al. |
| 5,425,745 A | 6/1995 | Green et al. |
| 5,478,344 A | 12/1995 | Stone et al. |
| 5,497,540 A | 3/1996 | Venkataramani et al. |
| 5,569,968 A | 10/1996 | Lal et al. |
| 5,630,837 A | 5/1997 | Crowley |
| 5,728,089 A | 3/1998 | Lal et al. |
| 5,865,361 A | 2/1999 | Milliman et al. |
| 5,905,628 A | 5/1999 | Okuno et al. |
| 5,915,616 A | 6/1999 | Viola et al. |
| 5,964,394 A | 10/1999 | Robertson |
| 5,985,065 A | 11/1999 | Kling |
| 6,001,069 A | 12/1999 | Tachibana et al. |
| 6,024,750 A | 2/2000 | Mastri et al. |
| 6,036,667 A | 3/2000 | Manna et al. |
| 6,059,799 A | 5/2000 | Aranyi et al. |
| 6,063,050 A | 5/2000 | Manna et al. |
| 6,063,098 A | 5/2000 | Houser et al. |
| 6,081,063 A | 6/2000 | Kasuga et al. |
| 6,090,120 A | 7/2000 | Wright et al. |
| 6,092,422 A | 7/2000 | Binnig et al. |
| 6,126,657 A | 10/2000 | Edwards et al. |
| 6,127,811 A | 10/2000 | Shenoy et al. |
| 6,159,207 A | 12/2000 | Yoon |
| 6,176,953 B1 | 1/2001 | Landreth et al. |
| 6,206,842 B1 | 3/2001 | Tu et al. |
| 6,231,565 B1 | 5/2001 | Tovey et al. |
| 6,254,622 B1 | 7/2001 | Hood |
| 6,254,623 B1 | 7/2001 | Haibel, Jr. et al. |
| 6,280,407 B1 | 8/2001 | Manna et al. |
| 6,288,534 B1 | 9/2001 | Starkweather et al. |
| 6,325,811 B1 | 12/2001 | Messerly |
| 6,328,751 B1 | 12/2001 | Beaupre |
| 6,340,352 B1 | 1/2002 | Okada et al. |
| 6,358,264 B2 | 3/2002 | Banko |
| 6,362,557 B1 | 3/2002 | Gruber et al. |
| 6,387,109 B1 | 5/2002 | Davison et al. |
| 6,413,255 B1 | 7/2002 | Stern |
| 6,416,486 B1 | 7/2002 | Wampler |
| 6,585,745 B2 | 7/2003 | Cimino |
| 6,589,200 B1 | 7/2003 | Schwemberger et al. |
| 6,666,875 B1 | 12/2003 | Sakurai et al. |
| 6,685,657 B2 | 2/2004 | Jones |
| 2002/0183774 A1 | 12/2002 | Witt et al. |
| 2002/0198555 A1 | 12/2002 | White et al. |

FOREIGN PATENT DOCUMENTS

| | | |
|---|---|---|
| EP | 0 738 501 A1 | 10/1996 |
| WO | 09952489 | 10/1999 |
| WO | 0105306 A1 | 1/2001 |

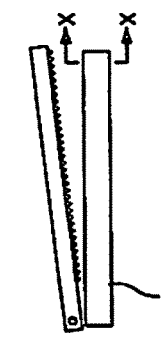
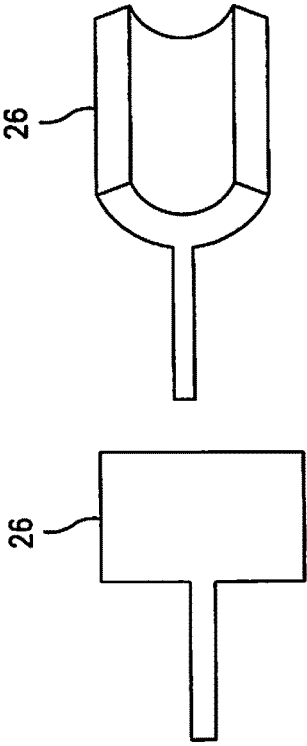
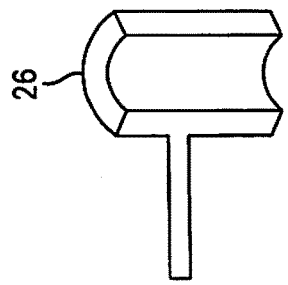
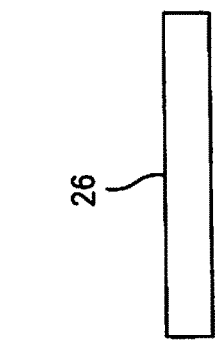
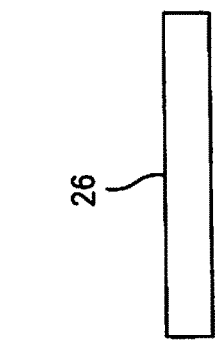

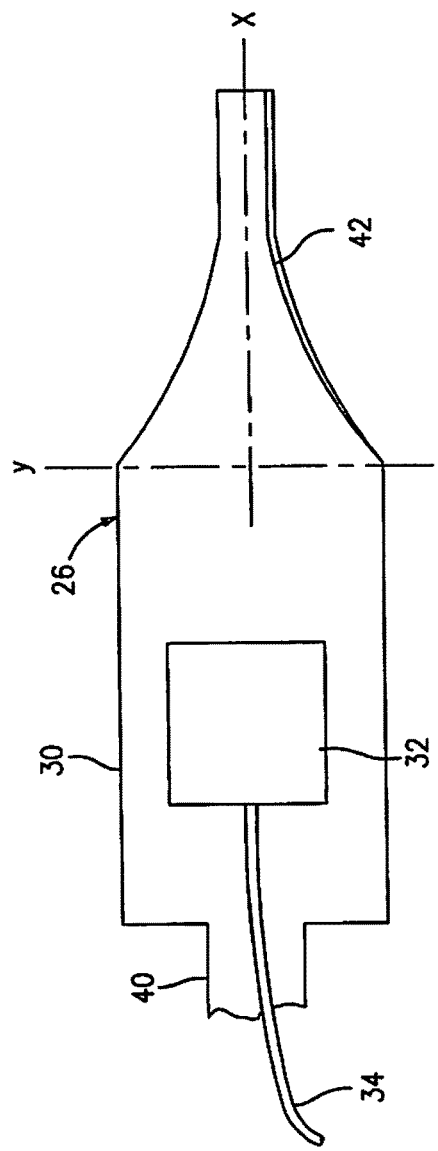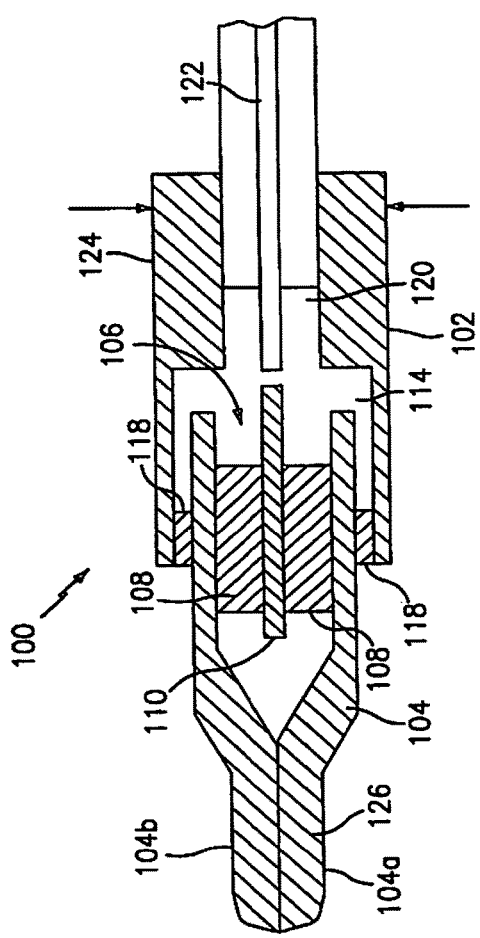

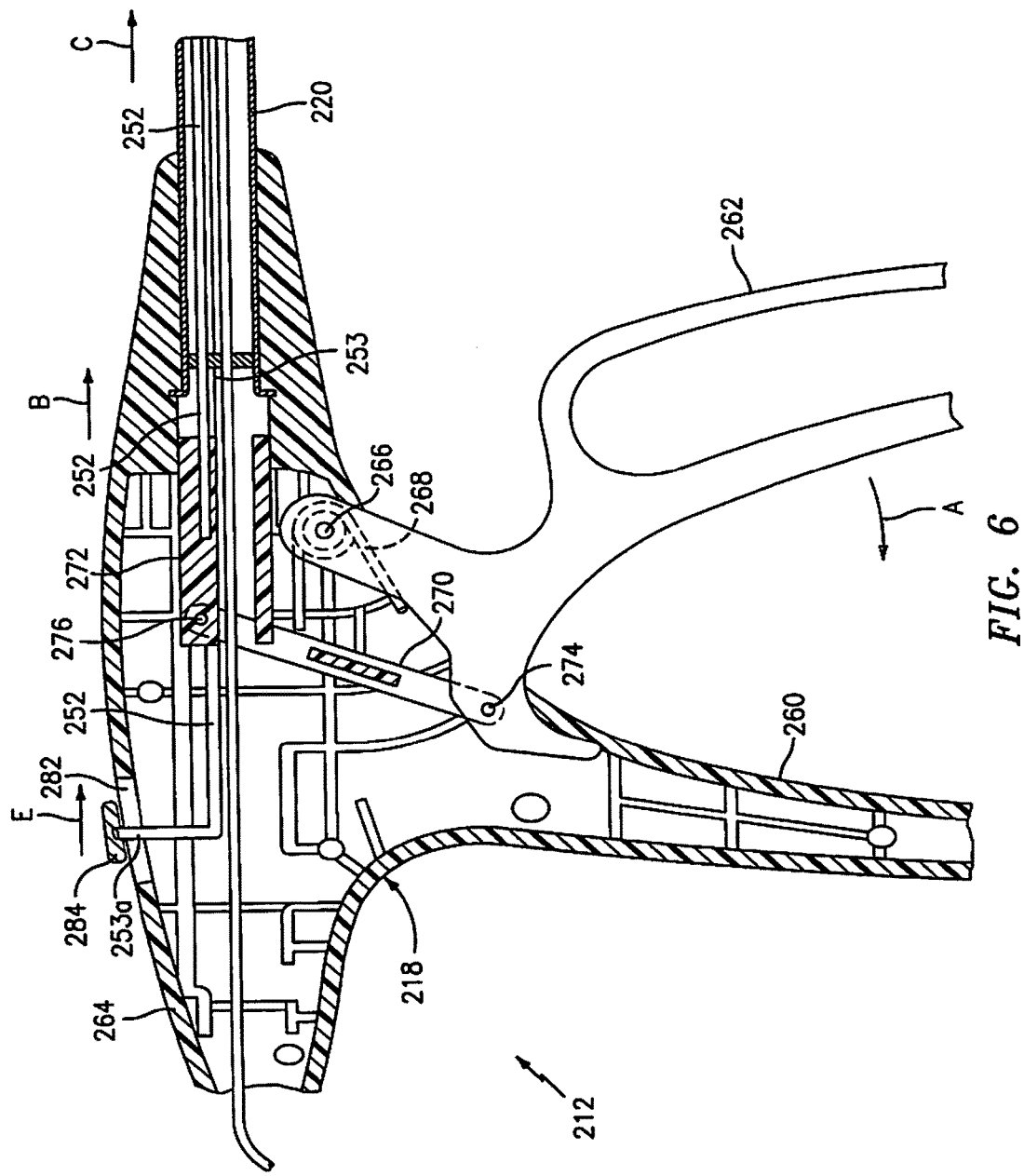

ULTRASONIC SURGICAL INSTRUMENT

CROSS-REFERENCE TO RELATED APPLICATIONS

This is a continuation of U.S. patent application Ser. No. 12/053,113, filed Mar. 21, 2008, (now abandoned), which is a continuation of U.S. patent application Ser. No. 10/467,512, filed Aug. 7, 2003 (now Abandoned), which is a 371 of PCT Patent Application Serial No. PCT/US2002/04988, filed Feb. 8, 2002, which claims priority to U.S. Provisional Application Ser. No. 60/267,251, filed Feb. 8, 2001, which is incorporated herein by reference in its entirety.

BACKGROUND

Technical Field

The present disclosure relates generally to ultrasonic surgical instruments. More specifically, the present disclosure relates to ultrasonic surgical instruments having an end effector configured to effect tissue dissection, cutting, coagulation, ligation and/or hemostatis and having a microelectromechanical system incorporated therein ("MEMS"), which instrument can be used in open as well as laparoscopic or endoscopic surgical procedures.

Background of Related Art

Ultrasonic instruments for surgical use are well known and are used in a variety of surgical procedures for dissecting, cutting, ligating, effecting coagulation in, and/or effecting hemostasis in tissue. Typically, ultrasonic surgical instruments include a handpiece for grasping the instrument, a transducer attached to the proximal end of the handpiece, and a vibration coupler extending from the transducer through a body of the instrument to an end effector of the instrument. The transducer generates vibrations in the ultrasonic frequency range which are transmitted from the handpiece of the instrument to the end effector via the vibration coupler. This configuration, although effective in some applications, has several drawbacks. For example, the power of the instrument is attenuated when ultrasonic energy is transmitted from a proximal end of a device to a distal end of the device. Further, power losses are enhanced at couplings and seals of the instrument. As such, a large, heavy transducer is required to operate known surgical instruments. Moreover, contact between the vibration coupler and stationary components of the instrument result in mechanical faults in the instrument. Finally, the vibration coupler acts as a pump which draws bodily fluids from the distal end of the instrument to the proximal end of the instrument thereby making sterilization of the instrument after use difficult.

The use of an elongated vibration coupler also limits the operational features of the instrument available to a surgeon. More specifically, because the vibration coupler transmits vibrations from the transducer to the end effector, the inclusion of an articulation joint into the vibration coupler is difficult and inefficient. Accordingly, known ultrasonic instruments typically do not include articulating end effectors. Moreover, because the vibrations are transmitted from the transducer at the proximal end of the instrument to the distal end of the instrument, along a stiff vibration coupler, e.g., an elongated titanium rod, vibration energy is transmitted primarily along the rod in longitudinal waves. Any transverse vibrations that do occur as the energy is transmitted along the length of the vibration coupler reduces the overall efficiency of the system.

SUMMARY

An ultrasonic surgical system is provided which includes a surgical instrument having an end effector with a transducer, a control module and a conductive cable interconnecting the surgical instrument to the control module. The control module is adapted to be connected to a power source, which may include an electrical outlet, an a/c generator, or a battery pack, etc., and includes control circuitry to drive the transducer positioned on the end effector of the instrument at an ultrasonic frequency or multiple ultrasonic frequencies independently or simultaneously. Alternately, the control circuitry may be incorporated into the power source. The ultrasonic instrument includes a handle assembly, a body portion and an integral or removable end effector configured to effect cutting, dissection, ligation, hemostasis and/or coagulation of tissue. The end effector includes an ultrasonic member which is preferably formed from a silicon composite, e.g., silicon-titanium composite material. The transducer is supported on, within or adjacent the ultrasonic member of the end effector. The ultrasonic member may have a variety of different configurations including different hook configurations, rectangular, circular, square, etc. The end effector may also include a clamp member or shear probe. In one preferred embodiment, the endoscopic body portion of the instrument is rotatable about its longitudinal axis to effect rotation of the end effector about the longitudinal axis of the endoscopic body portion. Alternately, the end effector or ultrasonic member may be rotatable independently of the endoscopic body portion of the instrument.

In another preferred embodiment, the surgical instrument includes an articulation member which can be pivoted about a pivot member positioned transverse to the longitudinal axis of the body portion using an articulation link. An end effector preferably including a transducer is secured to the articulation member and pivotable with the articulation member in response to reciprocation of the articulation link to effect articulation of the end effector, i.e., vary the angle of the end effector in relation to the longitudinal axis of the instrument.

BRIEF DESCRIPTION OF THE DRAWINGS

Various preferred embodiments of the presently disclosed ultrasonic surgical instrument are described herein with reference to the drawings, wherein:

FIG. 1A is a side view of one preferred alternate embodiment of the ultrasonic member of the presently disclosed ultrasonic instrument;

FIG. 1B is a side view of another preferred alternate embodiment of the ultrasonic member of the presently disclosed ultrasonic instrument;

FIG. 1C is a side view of another preferred alternate embodiment of the ultrasonic member of the presently disclosed ultrasonic instrument;

FIG. 1D is a cross-sectional view taken along section lines X-X in FIG. 1C;

FIG. 1E is a cross-sectional view of an alternate embodiment of the ultrasonic member shown in FIG. 1D as would be seen along section line X-X of FIG. 1C;

FIG. 1F is a cross-sectional view of another alternate embodiment of the ultrasonic member shown in FIG. 1D as would be seen along section line X-X of FIG. 1C;

FIG. 1G is a cross-sectional view of yet another alternate embodiment of the ultrasonic member shown in FIG. 1D as would be seen along section line X-X of FIG. 1C;

FIG. 1H is a top view of another alternate embodiment of the presently disclosed ultrasonic member;

FIG. 1I is a side perspective view of another embodiment of the presently disclosed ultrasonic member;

FIG. 1J is a side perspective view of another embodiment of the presently disclosed ultrasonic member, FIG. 1K is a side view of another embodiment of the presently disclosed ultrasonic member;

FIG. 2 is a schematic top representation of one preferred embodiment of the ultrasonic member of the presently disclosed ultrasonic instrument;

FIG. 5 is a top view of a preferred embodiment of an ultrasonic member of the presently disclosed ultrasonic surgical instrument;

FIG. 6 is a side cross-sectional view with portions broken away of a proximal portion of another preferred embodiment of the presently disclosed ultrasonic instrument.

DETAILED DESCRIPTION OF PREFERRED EMBODIMENTS

Figure 1:
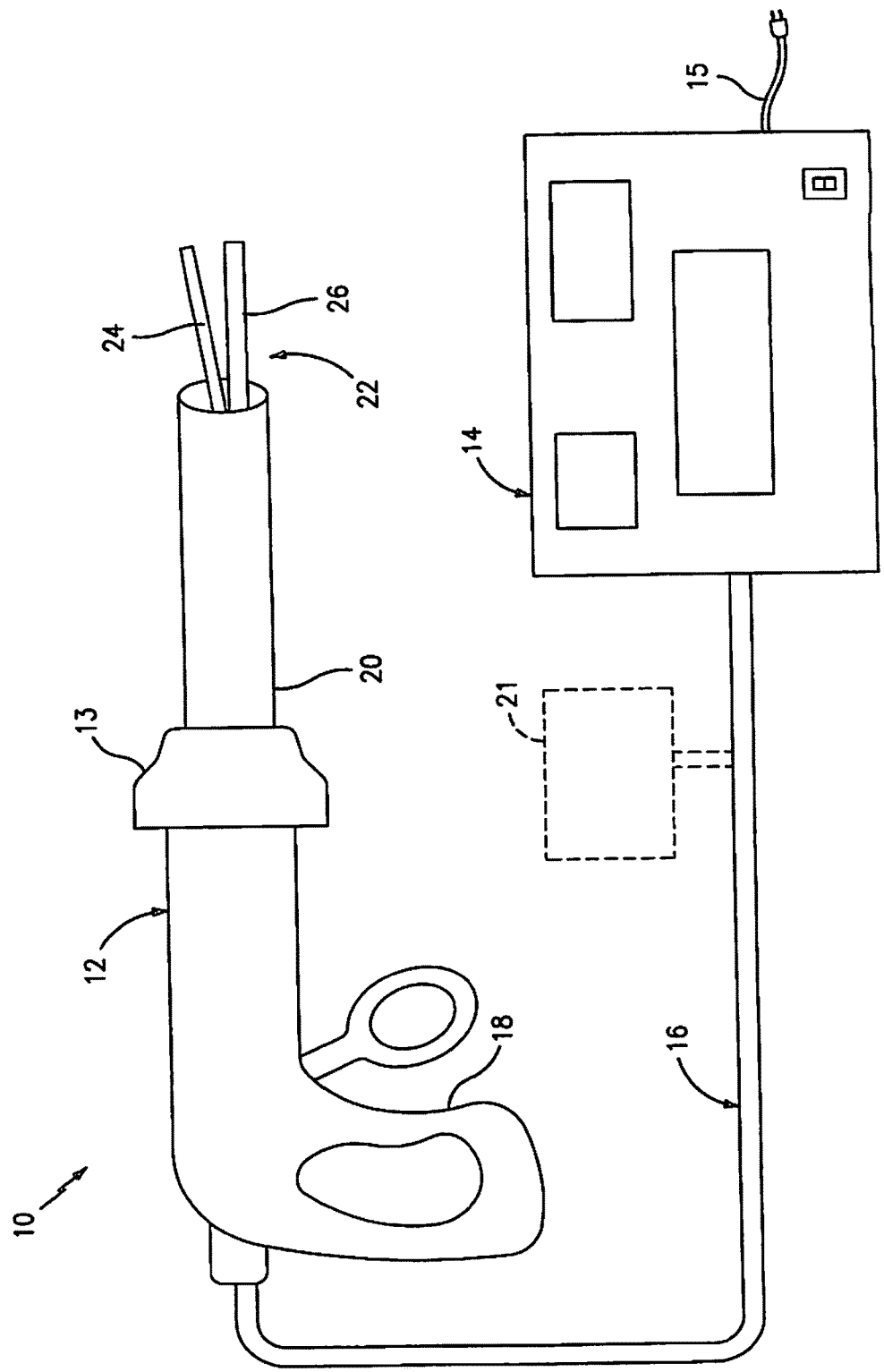
FIG. 1 is a schematic representation of one embodiment of the presently disclosed ultrasonic surgical system including a surgical instrument for cutting, dissecting, ligating, coagulating and/or effecting hemostasis in tissue.

Preferred embodiments of the presently disclosed ultrasonic surgical instrument will now be described in detail with reference to the drawings, in which like reference numerals designate identical or corresponding elements in each of the several views.

FIG. 1 illustrates a schematic view of an ultrasonic surgical system shown generally as 10. System 10 includes an ultrasonic instrument 12, a control module 14 and conductive cable 16 interconnecting instrument 12 to control module 14. Ultrasonic instrument 12 may be configured for open, endoscopic or laparoscopic surgical procedures and includes a handle assembly 18, an elongated body 20 and an end effector 22. Handle assembly 12 may have a pistol grip configuration, although other handle configurations are envisioned, e.g., in-line handle, pencil grips, standard scissor grips, new ergonomically designed grips, etc. Rotation knob 13 may be provided to facilitate rotation of elongated body 20 in a known manner. End effector 22 includes a pivotable clamp member 24 and a linear ultrasonic member 26. Alternately, the ultrasonic member of the end effectors may assume a variety of other configurations including, inter alia, J-hook (FIG. 1A), L-hook (FIG. 1B), shears (FIG. 1C) having a variety of different cross-sectional shapes (FIGS. 1D-1G), spatula (FIG. 1H), arcuate (FIGS. 1I and 1J) and rectangular (FIG. 1K). The end effector may also be configured to have a curved blade such as the blade disclosed in U.S. Pat. No. 6,024,750, filed on Aug. 14, 1997 and/or an angled blade, such as disclosed in U.S. Pat. No. 6,036,667, filed on Oct. 4, 1996, both of which are incorporated herein in their entirety by reference.

The ultrasonic member may be formed using an etching process, e.g., isotropic etching, deep reactive ion etching, etc. Suitable etching processes are disclosed in U.S. Pat. No. 5,728,089 filed Oct. 31, 1994, which is also incorporated herein in its entirety by reference. Alternately, other known means may be used to form the ultrasonic member including a variety of different mechanical processes.

As illustrated, control module 14 may include a power cord 15 for engagement with an electrical outlet (not shown). Alternately, module 14 may be adapted to receive power from a battery pack or from an a/c generator. It is also envisioned that a generator or other power source may be incorporated into control module 14.

Module 14 includes electronic control circuitry to drive a transducer (not shown) positioned on instrument 12 at one or more ultrasonic frequencies. Protective circuitry is provided to prevent injury to a patient, a surgeon or system hardware. Module 14 also includes display circuitry and hardware to provide information to and accept information from a user. This information may be obtained from sensors (not shown) positioned on the instrument end effector. The sensors may be provided to monitor the temperature or, ultrasonic or electric impedence, of the tissue being operated on. Feedback circuitry may be provided to interact with any sensors provided to provide more effective ligation, cutting, dissection, coagulation, etc. For example, the feedback circuitry may terminate operation of the system if a sensor indicates that tissue temperature or ultrasonic or electrical impedence has exceeded a predetermined maximum. The ultrasonic impedence increases as tissue hardens due to rising temperatures. Similarly, electrical impedence is reduced when tissue water level is decreased due to overheating. The feedback circuitry may be selectively activated and deactivated and/or controlled or monitored by a surgeon to provide a surgeon more flexibility in operating the instrument. Further, control module 14 may include diagnostic circuitry to aid in testing and/or debugging instrument 12 or its hardware.

It is contemplated that operation of ultrasonic instrument 12 may be automatically controlled through the use of a computer. In one preferred alternative embodiment of the presently disclosed system, a computer 21 receives data from sensors positioned on the end effector of the ultrasonic instrument. As discussed above, sensors may be provided to monitor different characteristics of the tissue being operated upon including, inter alia, temperature and/or ultrasonic or electrical impedence. Computer 21 preferably includes circuitry to process an analogue signal received from the sensor(s) and to convert the analogue signal to a digital signal. This circuitry may include means to amplify and filter the analogue signal. Thereafter, the digital signal can be evaluated and operation of the ultrasonic instrument can be modified to achieve the desired effect in or on the tissue and prevent damage to surrounding tissue. Computer 21 may be incorporated into control module 14 or linked to control module 14 to effect the desired or appropriate modification of the operation of the instrument 12.

FIG. 2 illustrates a top or side schematic view of ultrasonic member 26 of an end effector 22. Ultrasonic member 26 includes a body portion 30 which is preferably formed of components made of silicon material. Alternately, materials such as titanium or other metals may be bonded or joined in some manner to the silicon to improve fracture resistance. It is envisioned that materials other than silicon which are suitable for ultrasonic use may be used to form ultrasonic member 26. A transducer 32, preferably a piezoelectric transducer, is supported on, or bonded to or within ultrasonic member 26. Piezoelectric transducer 32 is connected to the power source and control module 14 by an electrical connector, preferably a cable 34. Cable 34 may extend proximally from transducer 32 through body 20 of instrument 12 (FIG. 1) and exit instrument 12 through an opening (not shown) in the handle assembly 18 of the instrument.

As discussed above, ultrasonic member 26 may assume a variety of different configurations (FIGS. 1A-1K) and may be attached to a distal portion of instrument 12 in any known manner. For example, ultrasonic member 26 may be secured to a substrate or shaft or a mounting member (not shown) supported within a distal end of body 20 of instrument 12 such as by a snap-fit connection, a set screw or crimping or swaging. A threaded shank 40 or other attachment structure formed on or disposed on or in a proximal end of member 26 may be provided for attachment of ultrasonic member 26 to the distal end of instrument 12.

Transducer 32 can be positioned on or within or adjacent ultrasonic member 26 to effect vibration along any axis, e.g., the x-axis, the y-axis or any axis in between the x and y axis. Ultrasonic member 26 includes an operating surface generally designated 42 configured to effect dissection, cutting, coagulation, ligation and/or to effect hemostasis of tissue. Alternately, ultrasonic member 26 may include multiple operating surfaces to perform different tasks, e.g., cutting and coagulation. System 10, including instrument 12, can be used in a variety of surgical applications including general procedures, gynecologic, urologic, thoracic, cardiac and neurologic surgical procedures. Instrument 12 may be configured to perform both endoscopic and open surgical procedures and may be actuated via a finger switch or a foot pedal in a known manner. The actuation device may include wireless transmission circuitry to effect actuation of instrument 12.

By providing a transducer on, in or adjacent the distal tip of the instrument, the following benefits can be realized: a) the need for an elongated vibration coupler formed of titanium is obviated substantially reducing the cost of the instrument; b) the length of the body portion of the instrument can be changed, e.g., shortened or lengthened, with virtually no consequential change in instrument performance, e.g., since the instrument vibration coupler has been replaced by an electrical conductor, the instrument need not be retimed, at considerable expense, after changes in body length; c) ultrasonic energy can be transferred to a patient more efficiently, thus lowering energy power requirements; d) the portion of the instrument that is disposable can be easily varied and may comprise only the instrument tip with a limited reuse handle, the entire instrument or any degree of disposability therebetween; e) because the handle assembly does not support the transducer, the handle assembly can be more economically configured; and f) the use of a small transducer on, in or adjacent the distal end of the instrument in place of a large transducer on the proximal end of the instrument substantially reduces the weight of the instrument and makes it easy to manage especially during delicate surgical procedures.

Figure 3:
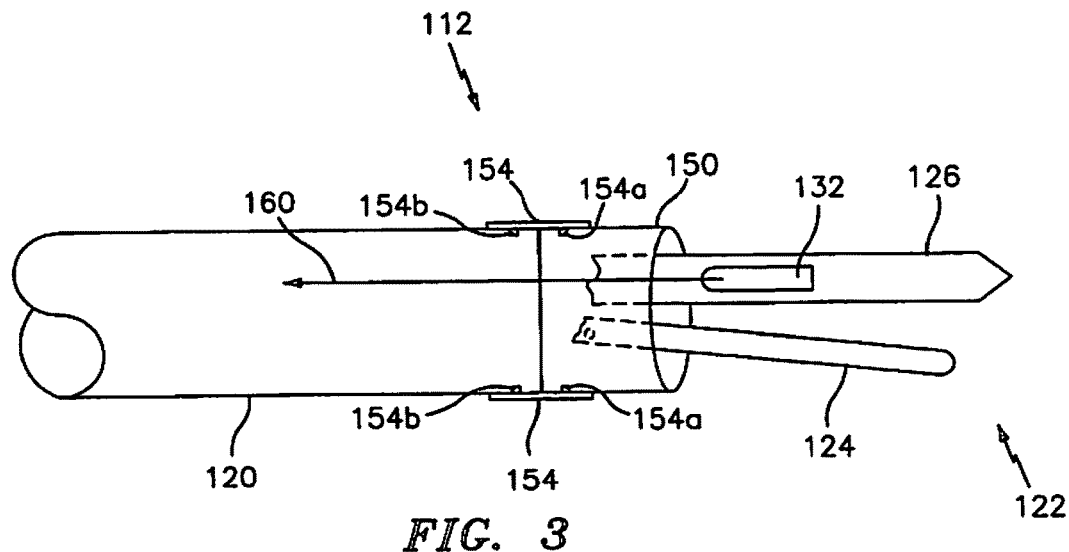
FIG. 3 is a side view with portions broken away of the distal end of another preferred embodiment of the presently disclosed ultrasonic surgical instrument including an articulating end effector.
Figure 4:
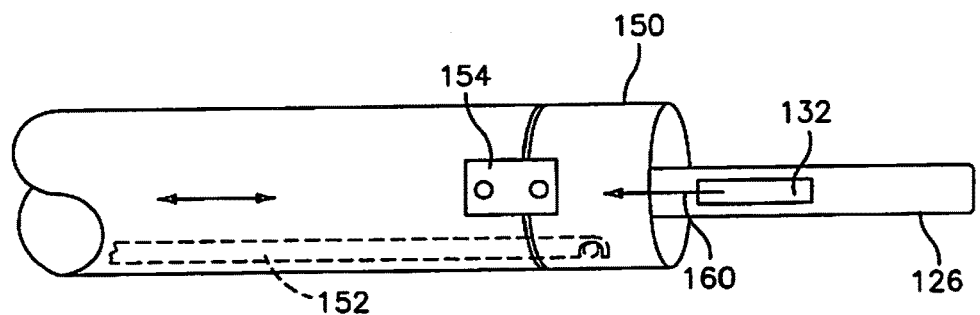
FIG. 4 is a top view with portions broken away of the distal end of the presently disclosed ultrasonic surgical instrument shown in FIG. 3.
Figure 4A:
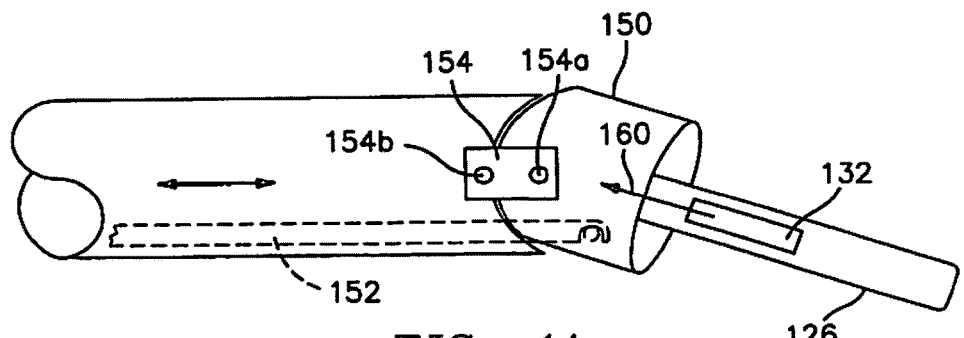
FIG. 4a is a top view with portions broken away of the distal end of the ultrasonic instrument shown in FIG. 4 in an articulated position.

FIGS. 3 and 4 illustrate the distal end of another preferred embodiment of the presently disclosed ultrasonic surgical instrument shown generally as 112. Instrument 112 includes an end effector 122 having an ultrasonic member 126 and a clamping jaw 124, a body portion 120 defining a hollow throughbore, an articulation member 150 and an articulation link 152 (FIG. 4). Ultrasonic member 126 includes a transducer 132. Preferably, the transducer is located as close to the distal end of ultrasonic member 112 as possible. A wire 160 interconnects transducer 132 to a power source (not shown). End effector 122 is supported within articulation member ISO and articulation member 150 is pivotably supported by members 154 about projections 154a to body portion 120. Articulation link 152 has a distal end which is pivotably connected to articulation member 150 at a location offset from pivot members 154. Articulation link 152 is linearly movable within body 120 to pivot member 150 about projections 154 to effect articulation of end effector 122. Articulation member 150 may be configured to effect articulation over an angle of between 5.degree. and 175.degree. and preferably between 30.degree. and 120.degree. Because transducer 132 is supported on ultrasonic member 126 of end effector 122, end effector 122 of ultrasonic instrument 112 can be articulated without interfering with the vibratory operation of the ultrasonic member (See FIG. 4A.).

FIG. 5 illustrates one preferred embodiment of an ultrasonic member, shown generally as 100, suitable for use in the presently disclosed ultrasonic surgical instrument of ultrasonic surgical system 10. Ultrasonic member 100 is preferably a piezoelectric laming structure which includes a frame 102, a resonant structure 104, and a transducer 106. Alternately, other transduction mechanisms, other than piezoelectric may be used. including thermal stress, electrostriction, magnetostriction or optical drive mechanisms. Transducer 106 preferably includes a pair of PZT crystals 108 separated by silicon plate 110. Alternately, it is envisioned that crystals other than PZT crystals may be used to convert electrical power to effect mechanical vibration. An appropriate bonding agent or process, e.g., solder bonding, diffusion bonding, adhesives, etc., is used to fasten crystals 108 to plate 110. Resonant structure 104 is preferably formed Scorn a silicon or metal resonant structure or a silicon/metal composite. Structure 104 preferably includes first and second resonant members 104a and 104b. The proximal end of members 104a and 104b together define a cavity for receiving transducer 106. Alternately, resonant structure 104 may be monolithically formed from a single piece of material. The mating surfaces of PZT crystals 108 and resonant members 104a and 104b are fastened together using an appropriate bonding agent or bonding process, e.g., glass binding, adhesives, etc. Frame 102 includes a body 112 which is preferably formed from a rigid material including metals, ceramics, etc. and includes a cavity 114 dimensioned and configured to receive the resonant structure 104 and transducer 106 assembly. A bonding layer or layers 118, preferably formed of a conductive material, is positioned between the proximal portion of resonant members 104a and 104b and frame 102 to bond transducer 106 which is movable to frame 102 which is stationary. The proximal end of frame 102 includes a throughbore 120 which is dimensioned to permit passage of an electrical conductor 122, e.g., a wire or coaxial cable, to provide power to transducer 106. The electrical conductor is preferably a high-voltage high-frequency Teflon insulator cable, although the use of other conductors is envisioned. The distal end of conductor 122 is connected to plate 110 by a flexible conductive wire 124 which does not restrict relative movement between frame 102 and transducer 106.

As discussed above, the shape of resonant structure 104 may be different than that shown in FIG. 5. More specifically, distal operating surface 126 of resonant structure 104 may assume any of the configurations shown in FIGS. 1A-1K or any other configuration not shown herein which may be advantageous for performing a particular surgical procedure. Moreover, a clamp may be provided to facilitate gripping of tissue.

Ultrasonic member 100 can be actuated in both high and low frequency ranges. In the low frequency range, approximately 20-100 KHz, the instrument will cause cavitation in tissue to effect cutting of the tissue. In the high frequency range, greater than 1 MHz, the instrument may be used for heating and coagulation of tissue. The high and low frequency actuation may occur simultaneously by an electronic power amplifier, capable of generating both frequencies. Providing multiple frequencies may provide improved cutting in tissue with reduced thermal spread and improved coagulation and hemostasis.

As discussed above, power losses and inefficiencies are substantially reduced as compared to conventional ultrasonic instruments by placing the ultrasonic energy generating PZT element adjacent, on or within the ultrasonic member of the end effector. Whereas conventional instruments may require 40-50 watts of electrical power to effect cutting of tissue, it is envisioned that the presently disclosed ultrasonic instrument will require only 20-30 watts of electrical energy to effect the cutting of tissue. Moreover, it is envisioned that the presently disclosed laminate structure of ultrasonic member 100 is operable at higher frequencies than conventional instruments. Because it is believed the use of higher frequencies may speed the rate of coagulation at a given power setting, the power requirements may be further reduced by operation of the instrument at higher frequencies.

Figure 7:
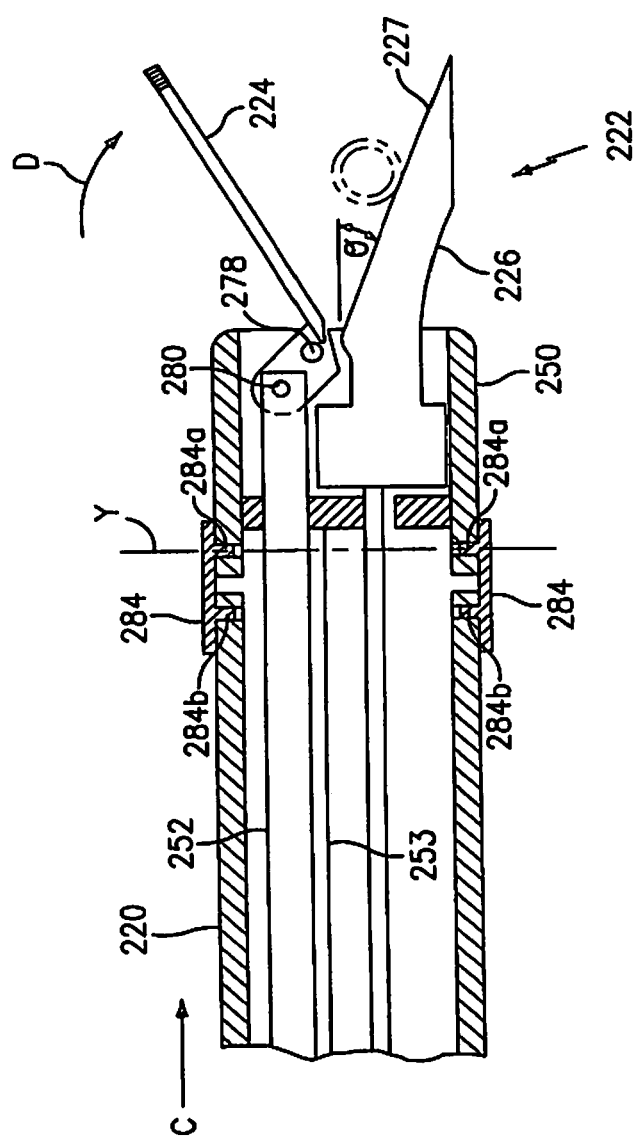
FIG. 7 is a side cross-sectional view with portions broken away of the distal end of the ultrasonic instrument shown in FIG. 6.

FIGS. 6 and 7 illustrate another preferred embodiment of the presently disclosed ultrasonic instrument shown generally 212. Ultrasonic instrument 212 includes a handle assembly 218 (FIG. 6), an elongated body 220 and an end effector 222 (FIG. 7). Handle assembly 218 includes a stationary handle portion 260 and a pivotable handle portion 262. Pivotable handle 262 is pivotably mounted to body portion 264 of handle assembly 218 about a pivot member 266 and is movable from a non-actuated position (FIG. 6) to an actuated position by moving handle 262 towards handle 260 against the bias of biasing member 268 in the direction indicated by arrow "A" in FIG. 6. A link 270 translates the pivotable movement of handle 262 to a linear drive member 272. Link 270 has a first end pivotably secured to pivotable handle 262 by a pin 274 and a second end pivotably secured to drive member 272 by a pin 276. Upon movement of pivotable handle 262 to the actuated position, linear drive member 272 moves in the direction indicated by arrow "B" in FIG. 6.

A flexible clamping rod or link 252 has a proximal end secured to drive member 272. Clamping link 252 is preferably formed of a shape memory or resilient material and has a distal end connected to a pivotable clamp member 224 (FIG. 7). Clamp member 224 is pivotably secured within a mounting member 250 by a pivot member 278. The distal end of clamping link 252 is pivotably connected to pivotable clamp member 224 by a pin 280 at a location offset from pivot member 278. In use, when handle 262 is moved in the direction indicated by arrow "A" (FIG. 6) to move drive member 272 in the direction indicated by arrow "B", clamp link 270 is advanced distally in a direction indicated by arrow "C" in FIGS. 6 and 7. Distal movement of clamp link 270 pivots clamp member 224 about pivot member 278 in the direction indicated by arrow "D" in FIG. 7 to a clamped position in juxtaposed alignment with ultrasonic member 226.

As illustrated in FIG. 6, an articulation link 253 is slidably positioned within body portion 264 of handle assembly 218.

Link 253 includes a proximal end 253a which extends through a slot 282 formed in body portion 264. A slide member 284 is secured to proximal end 253a of link 253 and is movable along the outer surface of body portion 264 in the direction indicated by arrow "E" to effect distal movement of articulation link 253.

Referring to FIG. 7, a mounting member 250 is pivotably secured to the distal end of elongated body 220 by pivot members 284. Pivot members 284 each include first and second projections 284a and 284b, respectively. Projections 284a are pivotably secured to elongated body 220 and projections 284b are pivotably secured to mounting member 250 such that mounting member 250 is pivotable with respect to elongated body 220 about a transverse axis Y. The distal end of articulation link 253 is engaged with a projection (not shown) extending outwardly from an inner surface of mounting member 250. The projection is laterally offset from pivot axis Y. When link 253 is moved distally or proximally, mounting member 250 is pivoted about pivot axis Y to an articulated position. See FIG. 4A. In a preferred embodiment, mounting member 250, and thus end effector 222, can be articulated over an arc of about 150.degree.

End effector 222 includes clamp member 224 and ultrasonic member 226. Ultrasonic member 224 is secured within mounting member 250 using any known fastening technique including crimping, swaging, screws, etc. Ultrasonic member 224, although shown schematically, is substantially the same as ultrasonic member 100, except operating surface 126 includes a blade configuration. As discussed above, when mounting member 250 is pivoted about axis Y by articulation link 253, end effector 222 including ultrasonic member 224 are also pivoted, i.e., articulated, about transverse axis Y.

It will be understood that various modifications may be made to the embodiments disclosed herein. For example, the configuration of the ultrasonic member of the end effector need not be as shown herein but rather may be modified to suit a particular surgical application. Further, the transducer may be mounted proximally of the ultrasonic member of the end effector in the distal end of the instrument and need not be mounted directly to the ultrasonic member. Therefore, the above description should not be construed as limiting, but merely as exemplifications of preferred embodiments. Those skilled in the art will envision other modifications within the scope and spirit of the claims appended hereto.

What is claimed:
1. A surgical instrument comprising:
a handle;
an elongated body portion extending distally from the handle; and
an end effector supported on the distal end of the elongated body portion, the end effector including an ultrasonic member, the ultrasonic member including:
a frame defining a first cavity therein;
at least one resonant member at least partially disposed within the first cavity, the at least one resonant member defining a longitudinal axis and a second cavity; and
a transducer disposed within the second cavity, the transducer including:
a plate oriented along the longitudinal axis; and
at least two piezoelectric crystals, each one of the at least two piezoelectric crystals disposed on a respective side of the plate and oriented along the longitudinal axis.

2. The surgical instrument according to claim 1, wherein the transducer effects vibration in a direction transverse to the longitudinal axis.

3. The surgical instrument according to claim 2, wherein the at least one resonant member is formed monolithically.

4. The surgical instrument according to claim 2, wherein the at least one resonant member is formed from a first resonant member and an opposed second resonant member.

5. The surgical instrument according to claim 2, wherein the at least two piezoelectric crystals are bonded to the at least one resonant member.

6. The surgical instrument according to claim 5, wherein the frame is formed from a rigid material selected from the group consisting of metallic and ceramic.

7. The surgical instrument according to claim 6, wherein the at least one resonant member is formed from silicon.

8. The surgical instrument according to claim 6, wherein the at least one resonant member is formed from a metallic material.

9. The surgical instrument according to claim 6, wherein the at least one resonant member is formed from a silicon/metal composite.

10. The surgical instrument according to claim 6, wherein the transducer is bonded to the at least one resonant member and the frame, such that the transducer is movable relative to the frame.

11. The surgical instrument according to claim 2, wherein the at least one resonant member includes an operating surface defined on a distal end thereof, the operating surface configured to effect dissection of tissue.

12. The surgical instrument according to claim 2, wherein the end effector further includes a clamping jaw rotatably disposed thereon, the clamping jaw rotatable relative to the at least one resonant member from a first, spaced apart position to a second, approximated position.

13. The surgical instrument according to claim 2, wherein the end effector includes a J-hook configuration.

14. The surgical instrument according to claim 2, wherein the end effector includes an L-hook configuration.

15. The surgical instrument according to claim 2, wherein the at least one resonant member includes a rectangular configuration.

16. The surgical instrument according to claim 2, wherein the at least one resonant member includes a spatula configuration.

17. The surgical instrument according to claim 2, further including an articulation member pivotably disposed on the distal end of the elongated body portion.

18. The surgical instrument according to claim 17, wherein the end effector is disposed on the articulation member, such that articulation of the articulation member effects articulation of the end effector.

* * * * *